United States Patent [19]

Ashikaga

[11] Patent Number: 5,215,644
[45] Date of Patent: Jun. 1, 1993

[54] DISSOLVED OXYGEN ELECTRODE WITH VERIFICATION SYSTEM

[75] Inventor: Kazuhiko Ashikaga, Kyoto, Japan
[73] Assignee: Horiba, Ltd., Kyoto, Japan
[21] Appl. No.: 798,623
[22] Filed: Nov. 26, 1991
[30] Foreign Application Priority Data
 Nov. 30, 1990 [JP] Japan .............................. 2-130856[U]
[51] Int. Cl.⁵ ............................................. G01N 27/26
[52] U.S. Cl. .................................... 204/412; 204/415;
                                                                204/431; 204/432
[58] Field of Search ................ 204/431, 432, 412, 415,
                                                                204/422, 423

[56] References Cited
U.S. PATENT DOCUMENTS
 4,900,422  2/1990  Bryan et al. ........................ 204/412
 5,098,547  3/1992  Bryan et al. ........................ 204/412

*Primary Examiner*—John Niebling
*Assistant Examiner*—Bruce F. Bell
*Attorney, Agent, or Firm*—Price, Gess & Ubell

[57] ABSTRACT

An improved oxygen sensing electrode assembly is provided with first and second electrodes mounted within a cavity of a housing substrate. An oxygen permeable diaphragm closes the cavity and contains an appropriate electrolyte solution. A third electrode is mounted in the cavity, while a fourth electrode is mounted on the exterior of the housing. The third and fourth electrodes can be activated to monitor the condition of the electrolyte whereby the operability of the electrode assembly can be verified during an oxygen sensing measurement.

8 Claims, 2 Drawing Sheets

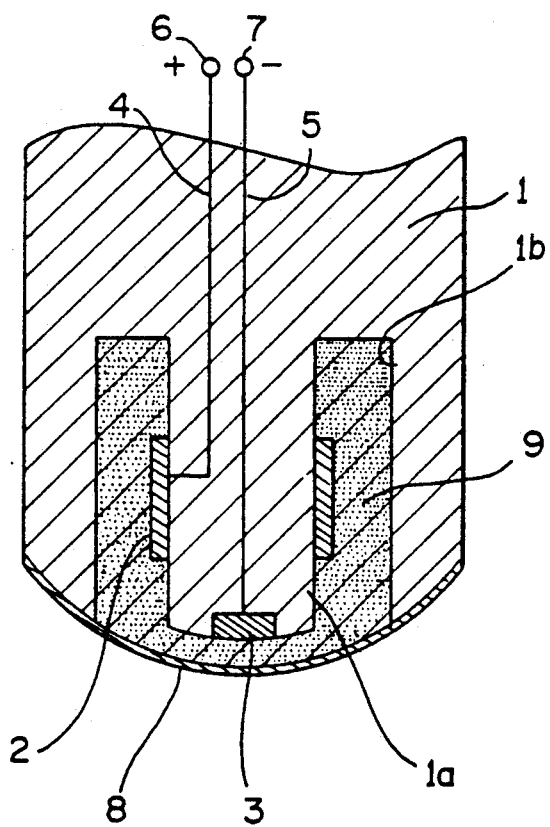

DISSOLVED OXYGEN ELECTRODE WITH VERIFICATION SYSTEM

BACKGROUND OF THE INVENTION

1. Field of the Invention

The present invention relates to an improved dissolved oxygen electrode for measuring a concentration of oxygen in a sample liquid and, more particularly, to a verification system to monitor its operability during use.

2. Description of Related Art

Conventional galvanic cell-type dissolved oxygen electrodes are frequently utilized to measure a concentration of oxygen in various sample liquids. A partial cross-sectional view of such a dissolved oxygen electrode is shown in FIG. 2.

A housing substrate 1 can be made of an insulating material, such as a synthetic resin, that will be inert to the fluids that it will encounter. The housing 1 can be formed into a cylindrical lower half portion having a central annular groove 1b that extends about an axial core portion 1a. The core portion 1a integrally extends from a central portion of the cylindrical lower half portion and is capable of supporting, for example, an annular anode 2 located on its outer circumferential surface. This anode 2 is connected with an appropriate terminal wire 6 that can extend outside of the housing 1 through a lead wire 4 arranged within the housing 1. An additional lead wire 5 is connected to another terminal 7 located outside of the housing 1, and extends to the lower tip of the axial core portion 1a. Cathode 3 can be mounted within a recess in the core portion 1a and connected to the lead wire 5 at this location. The entire lower end of the housing substrate 1 is covered with a diaphragm 8, of a known construction, that is permeable to oxygen. The inner hollow portion is thus formed between the diaphragm 8 and the annular groove 1b of the housing substrate 1. An appropriate electrolyte 9 can be sealed within this hollow portion 1b.

The dissolved oxygen electrode, when immersed in a sample liquid, can have oxygen from the sample liquid transmitted through the diaphragm 8, and subsequently be electrochemically reduced on a surface of the anode 2. This reaction will produce an electric current proportional to the concentration of oxygen in the sample liquid between the anode 2 and the cathode 3 through the electrolyte 9, which can be conveniently measured across the respective terminals 6 and 7 to provide a measurement signal proportional to the concentration of oxygen in the sample liquid.

If, during the use of the dissolved oxygen electrode, the diaphragm 8 becomes damaged, then the electrolyte 9 can either flow out of the housing 1 through the damaged portion of the diaphragm 8, or sample liquid can flow into the inner hollow portion 1b of the housing 1, to correspondingly contaminate the electrolyte 9. As a result, a value of electric current flowing between the anode 2 and the cathode 3 will be affected and will be generally reduced. In a conventional dissolved oxygen electrode, any damage to the diaphragm 8 may not be easily confirmed, so that a problem has frequently occurred in that the concentration of oxygen being measured will become erroneous since the operator may not know that there has been damage to the diaphragm 8. Additionally, the degree of damage to the diaphragm 8 may be progressive, and the resulting accuracy of the reading may also progressively deteriorate without being detected by the technician.

Efforts in the prior art to determine any damage to the diaphragm 8 have usually resulted from an estimate of the reduction of value of the electric current, but this generally required the necessity of specifying a sufficient reduction of the value of the electric current so that it would be observed as being outside of the range of the expected measurement. It may also require a testing procedure wherein the conventional dissolved oxygen electrode can be immersed in a specified sample, such as the atmosphere and a precalibrated saturate dissolved oxygen solution, in order to measure the value of the electric current. This calibration or testing procedure can be troublesome and can require the interruption of the actual measurement cycle of the dissolved oxygen electrode.

An additional problem occurs in that a reduction in the measured electric current can also occur as a result of a simple deterioration in the useful lifetime of both the anode 2 and the cathode 3. It is not always possible to determine if there has been damage to the diaphragm 8 or if the life cycle of the anode 2 and cathode 3 has been simply reduced through normal usage.

Thus, there is a demand in the prior art to provide an easy and economical verification system to determine the reliability of a dissolved oxygen electrode.

SUMMARY OF THE INVENTION

It is an object of the present invention to provide a dissolved oxygen electrode that is capable of efficiently and easily detecting any deterioration in its performance that can result from damage to its diaphragm.

A further object of the present invention is to provide a verification system that is relatively simple and easily incorporated into the structure of a dissolved oxygen electrode.

An additional object of the present invention is to provide a verification system that can provide a constant monitoring during the use of the dissolved oxygen electrode in its measurement operation.

In order to achieve the above-described objects, the present invention can be characterized as providing an exterior electrode on the outside of the housing member and second electrode position within an inner hollow portion of the housing member for operative contact with the electrolyte contained within the inner hollow portion 1b.

As a result of such a construction, if there is any damage to the diaphragm, an electrolyte either flows out of the housing through the damaged portion of the diaphragm, and/or sample liquid flows into the inner hollow portion. Then the respective interior and exterior electrodes of the verification system will record a significant change in the electrical resistance between them so that the existence of damage in the diaphragm can be confirmed through measurement of this electrical resistance independent of any deterioration of the oxygen measuring cathode and anode electrodes.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2 is a partial cross-sectional view showing a conventional dissolved oxygen electrode.

DESCRIPTION OF THE PREFERRED EMBODIMENTS

Figure 1:
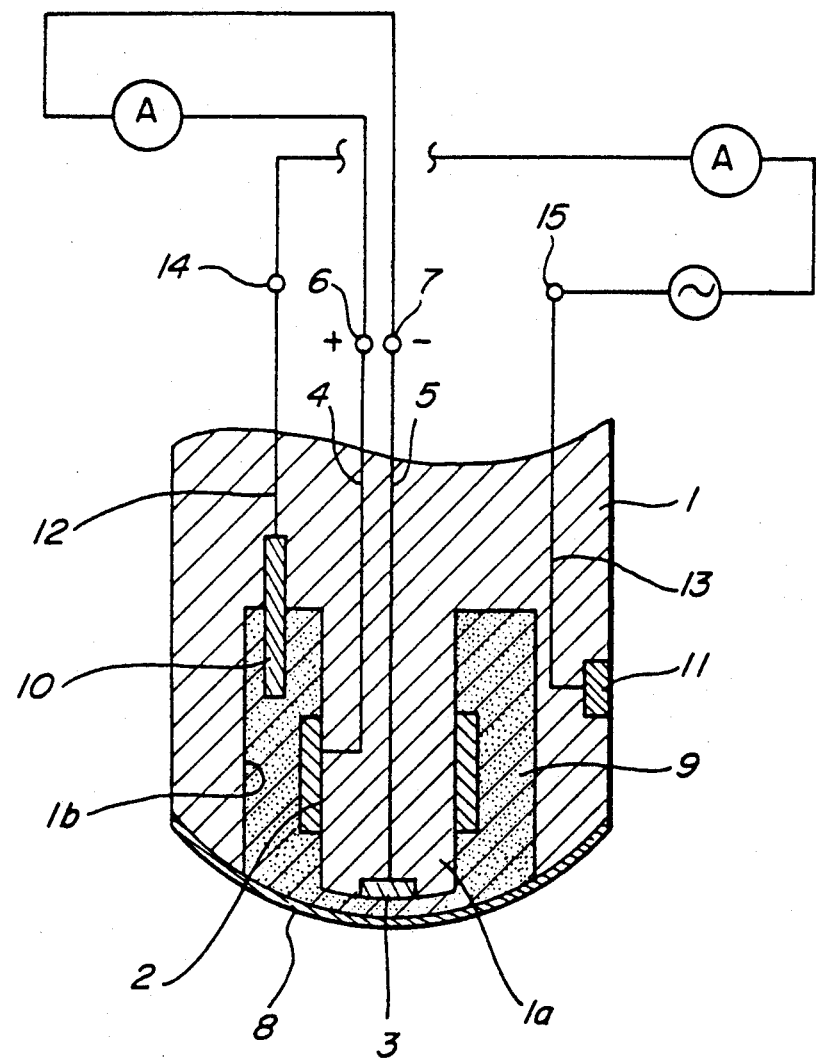
FIG. 1 is a partial cross-sectional view showing one preferred embodiment of a dissolved oxygen electrode with the verification system according to the present invention.

The following description is provided to enable any person skilled in the art to make and use the present invention and sets forth the best modes contemplated by the inventor of carrying out his invention. Various modifications, however, will remain readily apparent to those skilled in the art, since the generic principles of the present invention have been defined herein specifically to provide a relatively economical and easily manufactured dissolved oxygen electrode with a monitoring verification system.

Referring to FIG. 1, a partial cross-sectional view of an improved dissolved oxygen electrode according to the present invention is disclosed. In this preferred embodiment, a galvanic cell-type dissolved oxygen electrode has a housing 1, a measuring anode 2, a measuring cathode 3, and respective lead wires 4 and 5 connected to the anode 2 and cathode 3. The lead wires are also connected to exterior terminals 6 and 7, which can be connected to an appropriate monitor, as known in the art. A diaphragm 8 seals the electrolyte 9 within an interior inner portion 1b of the housing 1. As can be seen, these elements are similar to that of the conventional dissolved oxygen electrode, and similar reference numbers are accordingly utilized.

The housing 1 can be made of an insulating material, for example, a synthetic resin, and generally comprises a cylindrical lower half portion with its lower end open to provide a ring-like hollow with an axial core portion 1a integrally extending or juxtapositioned within the center of the cylindrical lower half portion. The axial core portion 1a is provided with an anode 2 made of, for example, platinum, gold, silver, and the like, which can extend about the outer circumferential surface of the axial core portion 1a. This anode 2 is connected with a terminal 6 outside of the housing 1 through an appropriate lead wire 4 arranged integrally within the housing 1.

The axial core portion 1a is further provided with a cathode 3 made of, for example, lead, zinc, and the like, at a lower end thereof. The cathode 3 is also connected with a terminal 7 exterior to the housing 1 through a lead wire 5, also arranged to extend integrally within the housing 1. A diaphragm 8 that is permeable to oxygen can be made of, for example, Teflon, polyethylene, and the like, as known in this art, and this diaphragm 8 can be sealed about the lower end opening of the housing 1 to form an interior chamber of an inner hollow portion 1b within the housing 1. The diaphragm 8 is sealed to the housing 1 to maintain an electrolyte 9, for example, an aqueous solution of sodium hydroxide, an aqueous solution of potassium chloride, and the like, as known in this art.

The verification system is designed specifically to be relatively economically integrated into the manufacture of a dissolved oxygen electrode. In this regard, a metallic electrode 10 is positioned within the housing 1 separately from the anode 2 so as to extend into the inner hollow portion 1b and to be brought into direct contact with the electrolyte 9. This electrode 10 is connected with a terminal 14, also positioned outside of the housing 1 through a lead wire 12 integrally arranged within the housing 1.

A second metallic electrode 11 can be mounted on an outer circumferential portion so that it is exposed and brought into direct contact with the sample liquid when the dissolved oxygen electrode is immersed in the sample. The metallic electrode 11 is connected with a terminal 15 positioned outside of the housing 1 through a lead wire 13 integrally arranged within the housing 1. The second and third metallic electrodes can be formed from a noble metal such as gold or silver, and also from a corrosive-resistant metal such as SUS (stainless steel).

The operation of the monitoring verification system will be capable of determining any damage to the diaphragm 8 in the dissolved oxygen electrode by responding to a change in the electrolyte, as follows:

An appointed direct current or alternating current voltage can be applied between the terminals 14 and 15 to activate the metallic electrodes 10 and 11 with the dissolved oxygen electrode immersed in a sample solution. A meter can appropriately measure the electrical resistance between the respective metallic electrodes 10 and 11 resulting from the value of the electric current flowing at this time. This value can establish the datum level of an operative and functioning diaphragm 8. If the diaphragm 8 is damaged, for example, by a collision with a foreign substance or an abrasion during transportation or mounting in a sample container to a degree that the electrolyte 9 within the inner hollow portion 1b of the housing 1 will be lost and/or sample liquid will flow into the inner hollow portion 1b of the housing. Then the electrical resistance between the metallic electrodes 10 and 11 will markedly change from that datum level.

As can be readily appreciated, this change in electrical resistance can be easily monitored and an appropriate indicator or an alarm (not shown) can be utilized to indicate the operative status of the dissolved oxygen electrode.

As can also be further appreciated, this measurement of the operability of the dissolved oxygen electrode can be carried out simultaneously with an actual measurement of the concentration of oxygen in a sample. Thus, oxygen from a sample fluid can be transmitted through the diaphragm 8 to be electrochemically reduced on a surface of the cathode 3. As a result, electric current proportional to the concentration of oxygen in the sample liquid will flow between the anode 2 and the cathode 3 through the electrolyte 9. An appropriate concentration of oxygen can be determined by the value of electric current between the terminals 6 and 7. Simultaneously, applying an appropriate current to the terminals 14 and 15 will permit a monitoring of any alteration in the resistance which will indicate a significant change in the status of the electrolyte 9 contained within the diaphragm 8.

As can be appreciated, a dissolved oxygen electrode can also include a polarograph-type electrode in addition to the above-described galvanic cell-type electrode. A polarograph-type dissolved oxygen electrode differs from the galvanic cell-type in that the appointed voltage is applied between the anode and the cathode during the time when the concentration of oxygen is measured. It is also possible to use the monitoring verification system in such a polarograph-type dissolved oxygen electrode.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved oxygen sensing electrode assembly comprising:
   a first electrode;
   a second electrode;
   a housing of an insulating material mounting the first and second electrodes in a cavity therein;
   an oxygen permeable diaphragm closing the cavity;
   an electrolyte contacting the first and second electrodes and sealed within the diaphragm closed cavity;
   a third electrode mounted in the cavity;
   a fourth electrode integrated within the housing to be partially mounted within the housing and partially exposed on the exterior of the housing, and
   means for activating the third and fourth electrodes to monitor the condition of the electrolyte, whereby the operability of the electrode assembly can be verified.

2. The electrodes assembly of claim 1 wherein the housing is molded of an insulating material.

3. The electrode assembly of claim 2 wherein connectors are embedded within the housing for each electrode.

4. The electrode assembly of claim 3 wherein the diaphragm is made of a plastic resin material.

5. The electrode assembly of claim 3 wherein the electrolyte is selected from a group consisting of an aqueous solution of sodium hydroxide and an aqueous solution of potassium chloride.

6. The electrode assembly of claim 4 wherein the diaphragm is made of Teflon.

7. An improved oxygen sensing electrode assembly comprising:
   a first electrode for measuring oxygen;
   a second electrode for measuring oxygen;
   a synthetic resin housing mounting the first and second electrodes in a cavity therein;
   an oxygen permeable diaphragm closing the cavity;
   an electrolyte contacting the first and second electrodes and sealed within the diaphragm closed cavity;
   a third electrode mounted in the cavity;
   a fourth electrode integrated mounted on the exterior surface of the housing; and
   means for activating the third and fourth electrodes, independent of the first and second electrodes, to monitor any change in electrical resistance of the electrolyte, whereby the operability of the electrode assembly can be verified.

8. An improved oxygen sensing electrode assembly comprising:
   a first electrode for measuring oxygen;
   a second electrode for measuring oxygen;
   a synthetic resin housing having a lower cavity with an integral core portion cantilevered into the cavity and mounting the first and second electrodes therein;
   an oxygen permeable diaphragm closing the cavity;
   an electrolyte contacting the first and second electrodes and sealed within the diaphragm closed cavity;
   a third electrode mounted in the cavity;
   a fourth electrode integrated mounted on the exterior surface of a side of the housing offset from the diaphragm; and
   means for activating the third and fourth electrodes, independent of the first and second electrodes, to monitor any change in electrical resistance of the electrolyte, whereby the operability of the electrode assembly can be verified.

* * * * *